(12) United States Patent
Rivera et al.

(10) Patent No.: US 6,475,175 B1
(45) Date of Patent: Nov. 5, 2002

(54) METHOD AND APPARATUS FOR SEQUESTERING PLATELET RICH PLASMA

(76) Inventors: John Rivera, 15191 E. Layton Pl., Aurora, CO (US) 80015; Son Le, 71 S. Chase Dr., Lakewood, CO (US) 80226; Daniel Cheek, 9201 S. Surgarstone Cir., Highlands Ranch, CO (US) 80126; Richard Matt, 7228 Clarendon St., San Jose, CA (US) 95129; Roger P. Kaminski, 20183 Aintree Ct., Parker, CO (US) 80134

( * ) Notice: Subject to any disclaimer, the term of this patent is extended or adjusted under 35 U.S.C. 154(b) by 0 days.

(21) Appl. No.: 09/288,145

(22) Filed: Apr. 8, 1999

Related U.S. Application Data

(62) Division of application No. 08/791,179, filed on Jan. 31, 1997, now Pat. No. 5,964,724
(60) Provisional application No. 60/010,939, filed on Jan. 31, 1996.

(51) Int. Cl.[7] .................. A61M 37/00; B01D 33/15; B01D 45/12; B04B 3/06
(52) U.S. Cl. .................. 604/6.02; 494/43; 494/37; 604/4.01; 604/6.11; 604/6.01; 422/44; 210/782
(58) Field of Search ............... 604/4–6, 4.01, 604/5.01, 6.01, 6.02, 6.04, 6.11, 6.1; 494/43–47, 56, 57, 3.7, 11; 128/898, 905; 210/739, 740, 745, 767, 780–82, 787

(56) References Cited

U.S. PATENT DOCUMENTS

| | | | | |
|---|---|---|---|---|
| 4,241,866 A | * | 12/1980 | Giesbert et al. | |
| 4,708,712 A | * | 11/1987 | Mulzet | 494/45 |
| 5,281,342 A | * | 1/1994 | Biesel | |
| 5,370,802 A | * | 12/1994 | Brown | |
| 5,505,685 A | * | 4/1996 | Antwiler | |
| 5,951,877 A | * | 9/1999 | Langley et al. | |

OTHER PUBLICATIONS

Blood Conservation Update; Electromedics, Inc./ University of Colorado Health Sciences Center Certificate Program; Spring–Summer 92; vol. 6:No. 2; pp. 16–19.

* cited by examiner

*Primary Examiner*—Angela D. Sykes
*Assistant Examiner*—Patricia Bianco
(74) *Attorney, Agent, or Firm*—Ancel W. Lewis, Jr.

(57) ABSTRACT

The present invention is a blood separation system that is fully mechanized to collect blood from a patient, separate waste portions of the blood, wash the blood, and redirect the usable portions to a device for reinjecting the usable portions into the patient. The present invention prevents accidental activation of an improper operation that could cause harm to a patient or a shut down of the system by requiring confirmation of each step by an operator. The invention provides screen displays with detailed setup instructions, eliminating the need for secondary documentation that might not be allowed in a surgical environment. The invention also instructs the operator at the appropriate times to do certain manual steps such as opening and closing clamps. Since the opening and closing of clamps is a highly critical operation, confirmation of these steps is also required. A method and suitable apparatus is also disclosed for sequestration of platelet rich plasma whereby a blood sample is spun at a high speed sufficient to separate solid cells from the blood sample and spun at a lower speed for a predetermined time to allow platelets to elute from the solid cells.

5 Claims, 18 Drawing Sheets

```
(AUTO   /STANDARD PROGRAM           <STOP>
FILL  WASH RATE  WASH VOL   EMPTY  CENT
300       300        1000       300    5600
[FILL}      [STANDBY]      [STOP]    [MENU]
(Push Fill to begin cycle)           10:00:00
```

Fig. 4A

```
Current Run Mode:          AUTO

[AUTO]            [MANUAL]

[ACCEPT]                             [CANCEL]
```

Fig. 4B

```
       DISPOSABLE SETUP
7.   Remove bowl and harness assembly, insert
     bowl in centrifuge plate, lock in place.
   [MORE]       [EXIT]
```

Fig. 4C

```
       DISPOSABLE SETUP
8.   Attach locking arms onto the bowl fill tube
     assembly and lock in place.
   [MORE]       [EXIT]
```

Fig. 4D

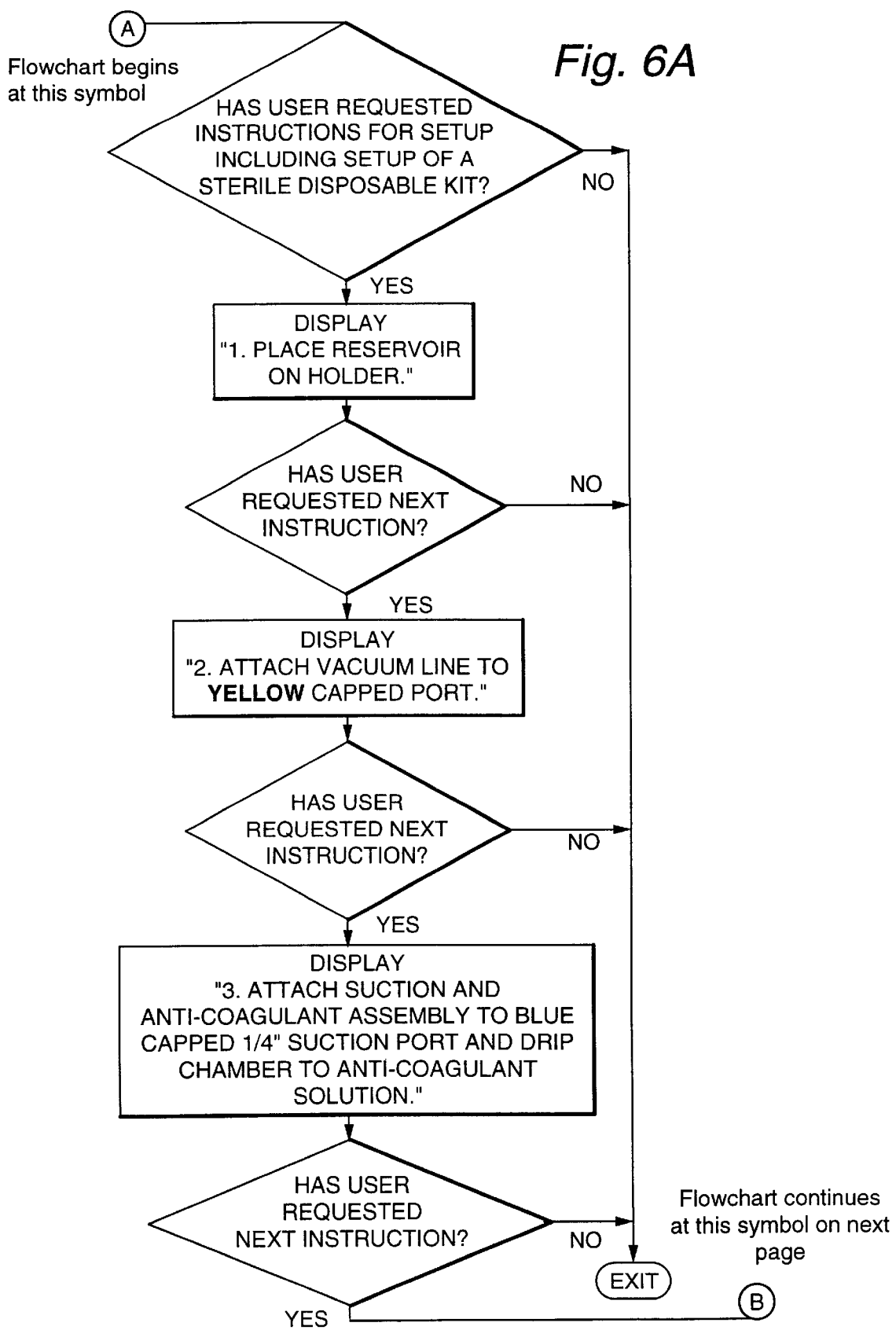

Flowchart continues at this symbol on next page

Flowchart continues at this symbol on next page

METHOD AND APPARATUS FOR SEQUESTERING PLATELET RICH PLASMA

This application is a division of Ser. No. 08/791,179, filed Jan. 31, 1997 now U.S. Pat. No. 5,964,734, and claims the benefit under 35 U.S.C. § 119(e) of the U.S. provisional patent application No. 60/010,939 filed Jan. 31, 1996.

TECHNICAL FIELD

The present invention relates to blood separation devices and methods in general and more particularly to blood separation devices and methods suitable for autotransfusion.

BACKGROUND ART

Surgical operations, including more complex operations where a substantial amount of bleeding may occur, may require transfusions during the course of the surgery to maintain a sufficient blood volume and blood pressure. Since many blood-borne diseases may exist including hepatitis, cancer and HIV, it is desirable to not require transfusion from another person. Also, if blood or blood components from the same person can be used, the necessity to match blood factors can be eliminated.

These disadvantages of receiving transfusions from donors are overcome by self-donation prior to operations. However, operations involving transfusions are not always identified in advance and few patients take the time and effort to go through the procedure. Additionally, a patient may be weakened by removal of blood prior to an operation.

Autotransfusion, whereby blood retrieved from the patient during the operation is separated so that reusable portions can be reinserted into the patient, is an effective method of overcoming the problems with transfusions. Various autotransfusion type systems currently exist but are somewhat complex to operate. For example, some autotransfusion systems require the operator to memorize a series of system steps to insure that the operator performs operations in the proper sequential order. Failure to perform the step or to perform the step in the proper sequence may cause the system to shut down or may cause morbidity in the patient.

Additionally, it is highly useful to have a blood separation system that can efficiently separate platelet and plasma from waste products in the blood. A high degree of efficiency in obtaining platelets has not been previously achieved.

It is therefore desirable to have a blood separation system that is highly efficient in extracting platelets from the blood, extracting waste products from the blood, allowing performance of operations in a simple and easy manner that does not require extensive knowledge of the system and processes, and preventing inadvertent or accidental operation of the blood separation device.

DISCLOSURE OF THE INVENTION

The present invention provides a blood separation system suitable for autotransfusion that displays instructions to guide the operator of the autotranfusion system to perform predetermined operation at predetermined times. In this manner, the operator of the system can be assured that the proper sequence of operations is being performed without a great degree of experience and knowledge of the system.

The present invention additionally requires confirmation of each operational step that is entered in the blood separation system by the operator to prevent the system from inadvertently being activated or performing an unintended operation that would necessitate the system being shut down or cause harm to the patient.

The present invention also is capable of separating blood platelets in a highly efficient manner from the blood sample by spinning the blood sample at a hard rate of approximately 5,600 rpm until the solid cells are separated from the blood sample, and then slowing the spin rate to a soft rate of about 2,400 rpm to allow the platelets to elute from the solid cells. The spin rate of 2,400 rpm is maintained for a period of approximately 60 seconds which allows the platelets to elute in a highly efficient manner.

BRIEF DESCRIPTION OF THE DRAWINGS

Details of this invention are described in connection with the accompanying drawings that bear similar reference numerals in which:

FIGS. 4A, 4B, 4C & 4D are representative views of screen displays of a blood separation system embodying the present invention.

FIGS. 6A, 6B, 6C, 6D, 6E, 6F, 6G, & 6H, 6I, 6J, 6K, 6L and 6M are flow charts of a software program for a central processing unit for a blood separation system embodying the present invention.

DETAILED DESCRIPTION OF THE INVENTION

Figure 1:
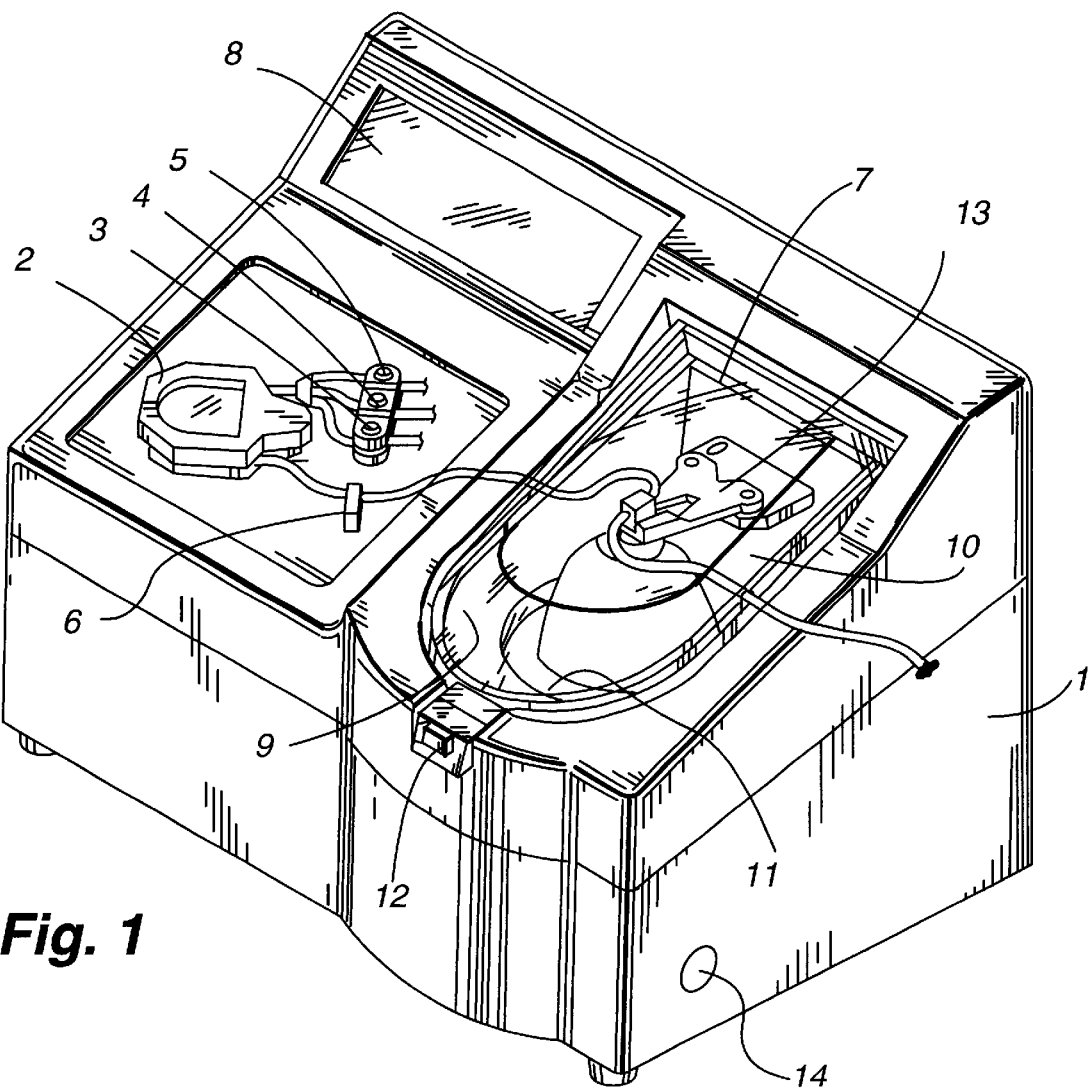
FIG. 1 is a perspective view of a blood separation system embodying the present invention.

Referring now to FIG. 1 there is shown a blood separation system embodying features of the present invention including a housing 1, a peristaltic pump 2, first, second, third clamps 3, 4, 5, an air bubble sensor 6, a centrifuge 7, and a touch sensitive control screen 8. The housing 1 is in general hexahedral or block shaped with vertical front wall, back wall, right side wall and left side wall, horizontal bottom wall, and top wall sloping downward from back to front.

The centrifuge 7 includes a centrifuge housing 9, a centrifuge cover 10, centrifuge drive means 11, a centrifuge latch 12, an upper centrifuge bowl clamp 13 and a drain port 13. The centrifuge 7 is mounted within the right half of housing 1 and is vibrationally isolated from housing 1. The top edge of centrifuge housing 9 slopes downwardly and forwardly so that the top edge is planar with the top surface of housing 1 when centrifuge 7 is installed in housing 1. Centrifuge cover 10 is a shatter resistant transparent dome, convex up, pivotally attached to the back of centrifuge housing 9, shaped so that the lower edge of centrifuge cover 10 covers the exterior of the top edge of centrifuge housing 9 forming a baffle and seals centrifuge 7 when centrifuge cover 10 is closed. Centrifuge latch 12 is attached to the front of centrifuge housing 9 and centrifuge cover 10, and retains centrifuge cover 10 in a closed position whenever centrifuge 7 is operating.

Centrifuge drive means 11 is mounted in the bottom of centrifuge housing 9 and is variable speed, rotating between about 1000 rpm and 6000 rpm in 100 rpm increments. Upper centrifuge bowl clamp 13 is rigidly attached to the back wall of centrifuge housing 9. Drain port 14 exits the centrifuge housing 9 at the lower right side, extending to the right side of housing 1, providing drainage of washing/cleaning liquid during maintenance and drainage of blood component if the centrifuge bowl breaks.

Pump 2 is rigidly attached to left, forward portion of the top of housing 1 with the inlet and outlet of pump 2 generally directed away from the front, left corner of the top of housing 1. Pump 2 is reversible and variable speed with capacity to pump between about 10 ml/min. and 1000 ml/min.

First, second, third clamps 3, 4, 5 are rigidly attached to the top of housing 1 adjacent to the inlet to pump 2. Clamps 3, 4, 5 are color coded, first clamp 3 blue, second clamp 4 yellow and third clamp 5 red. Air bubble sensor 6 is rigidly attached to the top of housing 1 adjacent to the outlet to pump 2.

Touch sensitive control screen 8 is mounted in housing 1 at the rear, left portion of the top of housing 1, facing toward the front of housing 1.

Figure 2:
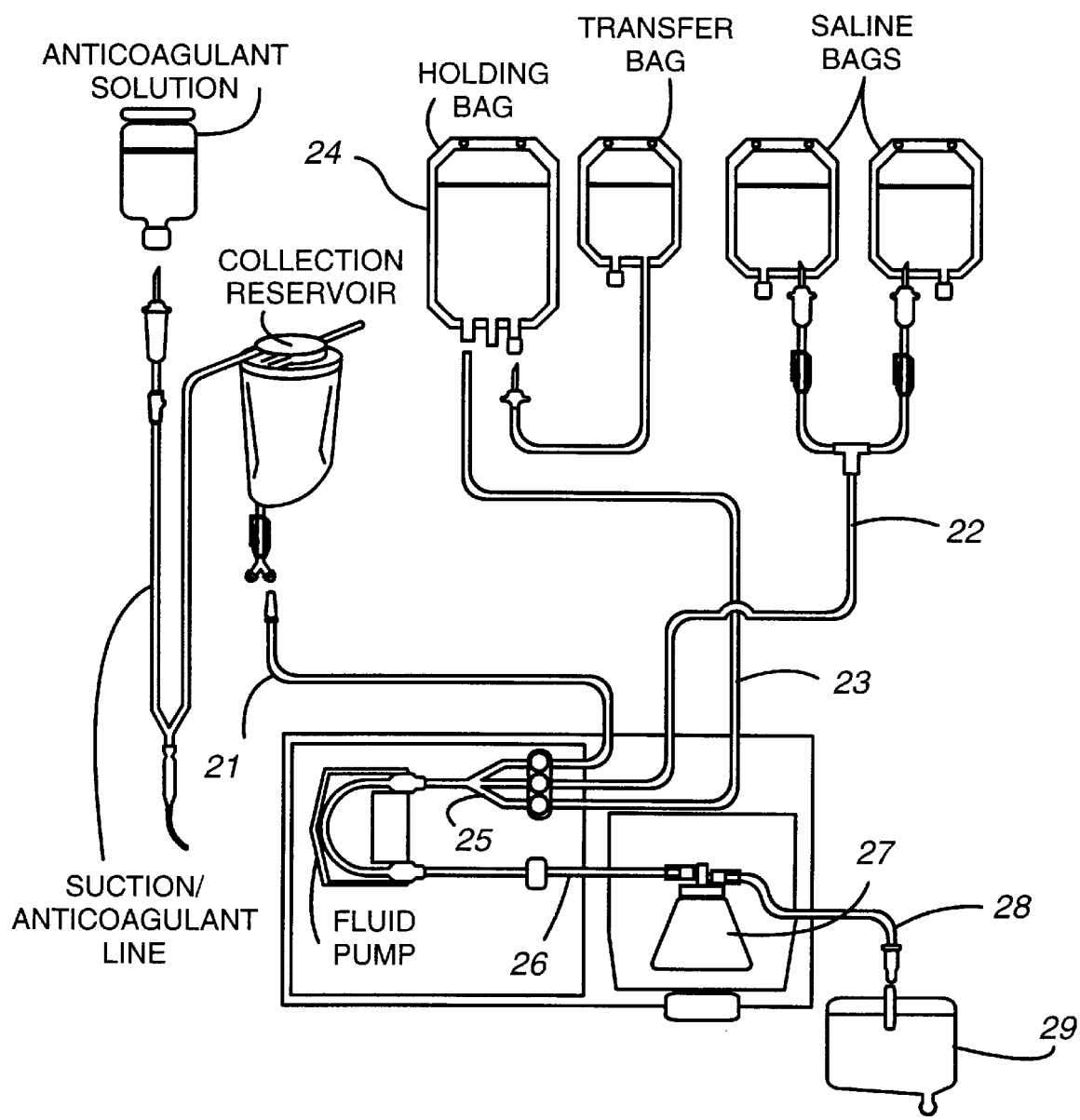
FIG. 2 is a diagram showing the sterile, disposable components of a blood separation system embodying the present invention.

Referring to FIG. 2, a blood processing kit includes the disposable components of the blood separation system, including blood source tubing 21, saline wash tubing 22, processed blood tubing 23, processed blood holding bag 24, a first 4-way connector 25, pump header tubing 26, a centrifuge bowl 27, centrifuge exit tubing 28 and waste bag 29. Blood source tubing 21 is color coded blue, connecting to the source of the blood to be processed at a first end, passing through third clamp 5, and connecting to the first 4-way connector 25 at the second end. Saline wash tubing 22 is color coded yellow, connecting to a saline source at a first end, passing through second clamp 4, and connecting to the first 4-way connector 25 at the second end. Processed blood tubing 23 is color coded red, connecting to processed blood holding bag 24 at a first end, passing through first clamp 3, and connecting to the first 4-way connector 25 at the second end. Pump tubing header connects to first 4-way connector at a first end, passes through pump 2, air bubble sensor 6 and the left edge of centrifuge cover 10, and connects to centrifuge bowl 27 at the second end.

Centrifuge bowl 27 is installed in centrifuge 7, the base of centrifuge bowl 27 being held and rotated by centrifuge drive means 11 and the top of centrifuge bowl 27 being stabilized by upper centrifuge bowl clamp 13. Centrifuge exit tubing 28 connects to centrifuge bowl 27 at a first end, passes through the right edge of centrifuge cover 10, and connects at a second end to waste bag 29 which hang on the right side of housing 1.

Figure 3:
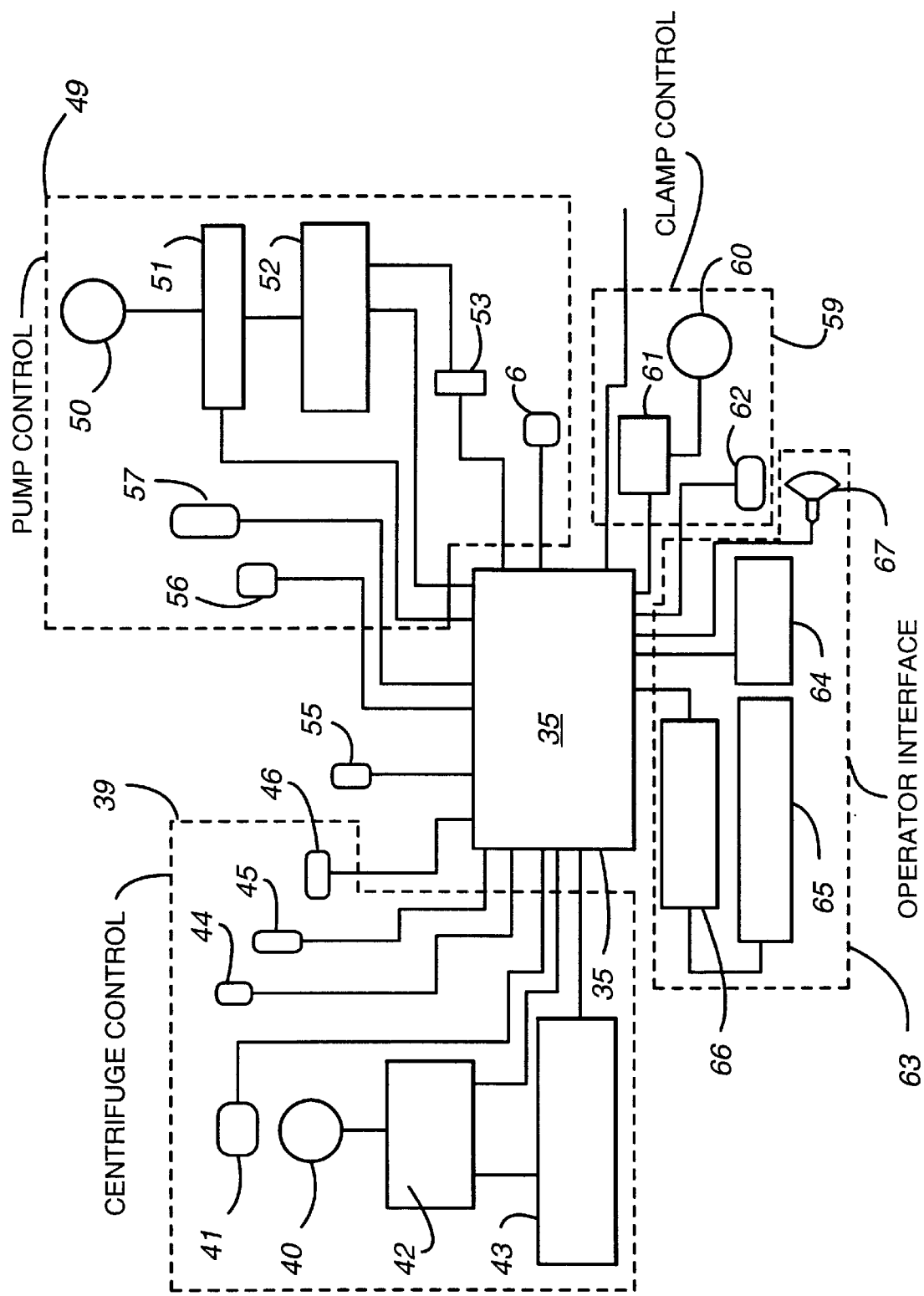
FIG. 3 is control system diagram of a blood separation system embodying the present invention.

FIG. 3 shows the control system for a blood separation system embodying the present invention. The control system includes centrifuge control 39, pump control 49, clamp control 59, operator interface 63 and system controller that is central processing unit 35.

Centrifuge control 39 has a centrifuge motor 40 that rotates the centrifuge drive means 11, a centrifuge motor controller 43 and centrifuge brake controller 42 that control the speed of rotation of centrifuge motor 40, a centrifuge hall sensor 41 and a centrifuge encoder 44 that independently monitor the speed of rotation of centrifuge motor 40, a centrifuge cover sensor 46 that senses whether centrifuge cover 10 is closed, and a centrifuge cover lock 45 that locks centrifuge latch 12 whenever centrifuge motor 40 is rotating above about 60 rpm.

Pump control 49 includes pump motor 50 that drives pump 2, pump relay 51 that supplies power to pump motor 50, pump motor controller 52 that controls the speed and direction of pump motor 50, pump hall sensor 57 and pump encoder 56 that independently monitor the speed and direction of rotation of pump motor 50, pump lid sensor 53 that senses whether the pump cover is closed, air bubble sensor 6 that senses whether fluid or air is flowing through pump header 26, and level sensor 55 which signals when centrifuge bowl 27 is full of red cells.

Clamp control 59 includes clamp motor 60 which opens and closes first, second and third clamps 3, 4, 5, clamp motor controller 61 which controls clamp motor 60, and clamp position sensor 62 that determines the position of first, second and third clamps 3, 4, 5.

The operator interface 63 includes a speaker 67 and the touch sensitive control screen d which has a display 64, touch screen 65 and touch screen controller 66. Touch screen 65 is transparent, physically mounts over the display 64, and provides operator input to the blood separation system. Display 64 is a 40 character by 6 line green fluorescent screen, and provides output and operator instructions. FIG. 4 shows examples of screen displays. Speaker 67 sounds an alarm signal when an alarm condition occurs in the blood separation system.

Central processing unit 35 coordinates the operation of the blood separation system, operating the pump 2, clamps 3, 4, 5, and centrifuge 7 in the proper sequence, direction and speeds, preventing pump 2 operation if the pump cover is open, preventing centrifuge 7 operation if the centrifuge cover 10 is open, locking centrifuge latch 12 when centrifuge 7 is rotating above about 60 rpm, monitoring fluid flow through air bubble sensor 6, and displaying system status, pump volume and centrifuge speed during operation. Referring to FIGS. 4C and 4D, central processing unit 35 also provides a series of tutorial screens that guide the operator, step by step, through the setup of the disposable components of a blood processing kit, and screens showing the details of each alarm condition when such alarm condition occurs. Referring to FIG. 4A and 4B, after an operator selects an operation on touchscreen 65, central processing unit 35 requires the operator to "accept" the selection by touching the ACCEPT position on touchscreen 65 before the blood separation system will proceed.

Central processing unit 35 has six preprogrammed software programs in ROM (Read Only Memory) including a Standard Program, Program A/trauma type applications, Program B/orthopedic applications, Program C/small volume applications, Program D/salvage type applications, and CONPLT/Concentrated Platelet Rich Plasma Sequestration. Programs A, B, C, D and CONPLT may be permanently reprogrammed by the operator, changes being stored in non-volatile RAM (Random Access Memory) maintained by battery back-up. The Standard Program and Programs A, B, C, D, CONPLT may be temporarily changed, the changes being lost when the blood separation system is turned off.

The Standard Program and Programs A, B, C, D may be run in "Automatic" mode. When "Automatic" mode is selected the blood separation system will proceed through the following steps without operator input. The first cycle is the fill cycle which starts with closing first clamp 3 and second clamp 4, and opening third clamp 5. The centrifuge drive means 11 begins to rotate, spinning centrifuge bowl 27. When centrifuge 7 reaches about 5100 rpm pump 2 starts to pump unprocessed blood into centrifuge bowl 27. As the centrifuge bowl 27 fills with blood, the heavier red cells are forced to the outside of centrifuge bowl 27 by centrifugal force while the lighter, undesirable components of the blood are forced inward, up and out of centrifuge bowl 27 through centrifuge exit tubing 28 to waste bag 29. When level sensor 55 detects that centrifuge bowl 27 is full of red cells the fill cycle ends.

The wash cycle starts with third clamp 5 closing, second clamp 4 opening and pump 2 beginning to pump saline wash into centrifuge bowl 27. After a predetermined period of time the wash cycle terminates, and pump 2 and centrifuge 7 stop. The empty cycle begins and pump 2 begins to pump fluid out of centrifuge bowl 27. A small predetermined volume of fluid is backflushed into saline tubing 22, then second clamp 4 closes and first clamp 3 opens so that the remaining washed red cells are pumped through the processed blood tubing 23 to holding bag 24 to await transfer to a transfer bag for reinjection into the patient.

The Standard Program and Programs A, B, C, D may also be run in "Semi-Automatic" mode. The blood separation system in "Semi-Automatic" mode follows the above sequence of steps but enters a standby mode at the end of the fill cycle and the end of the wash cycle, requiring operator selection of the next cycle before proceeding.

Figure 5:
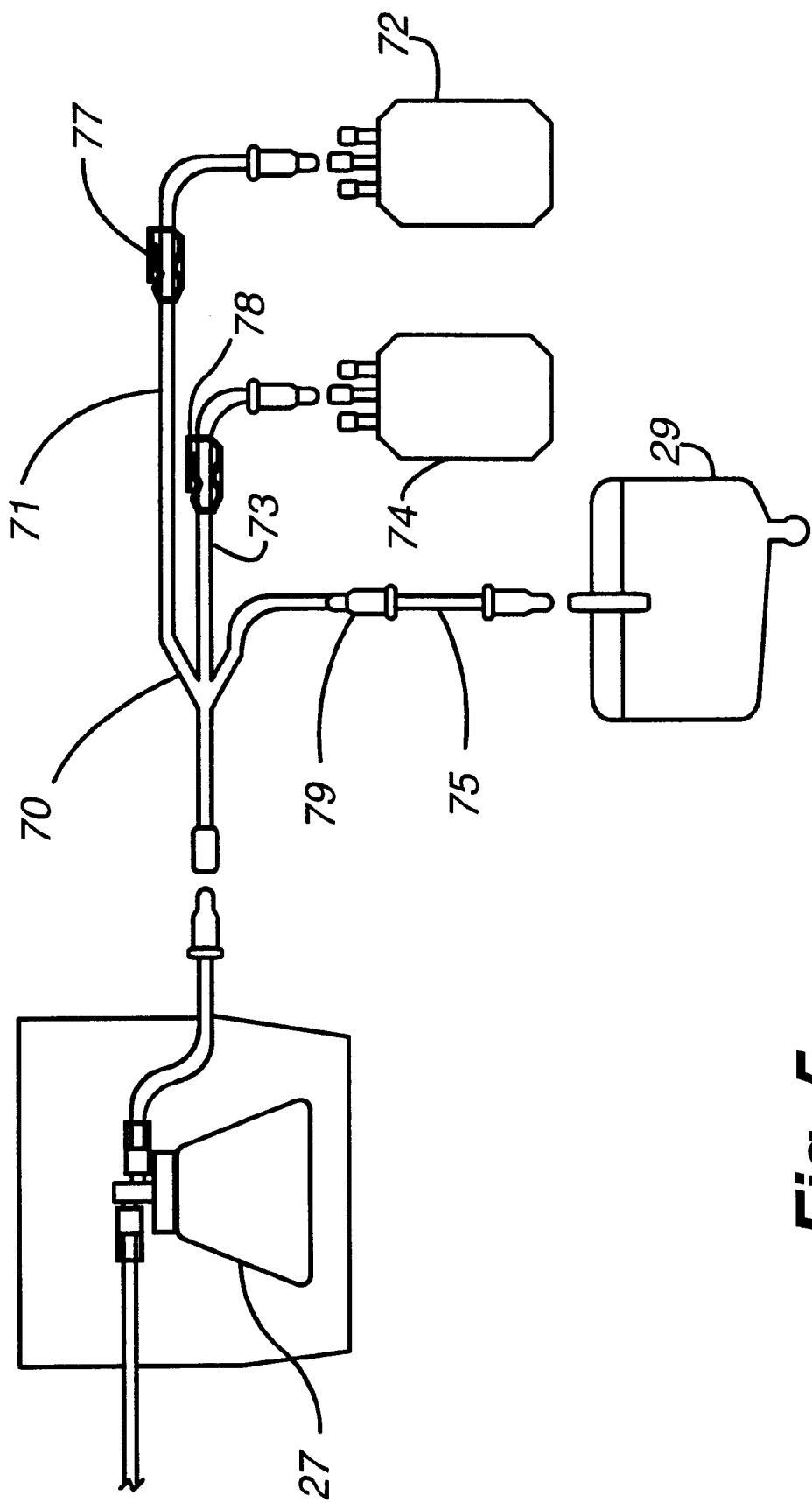
FIG. 5 is a diagram showing the sterile, disposable components for platelet rich plasma sequestration for a blood separation system embodying the present invention.
Figure 6B:
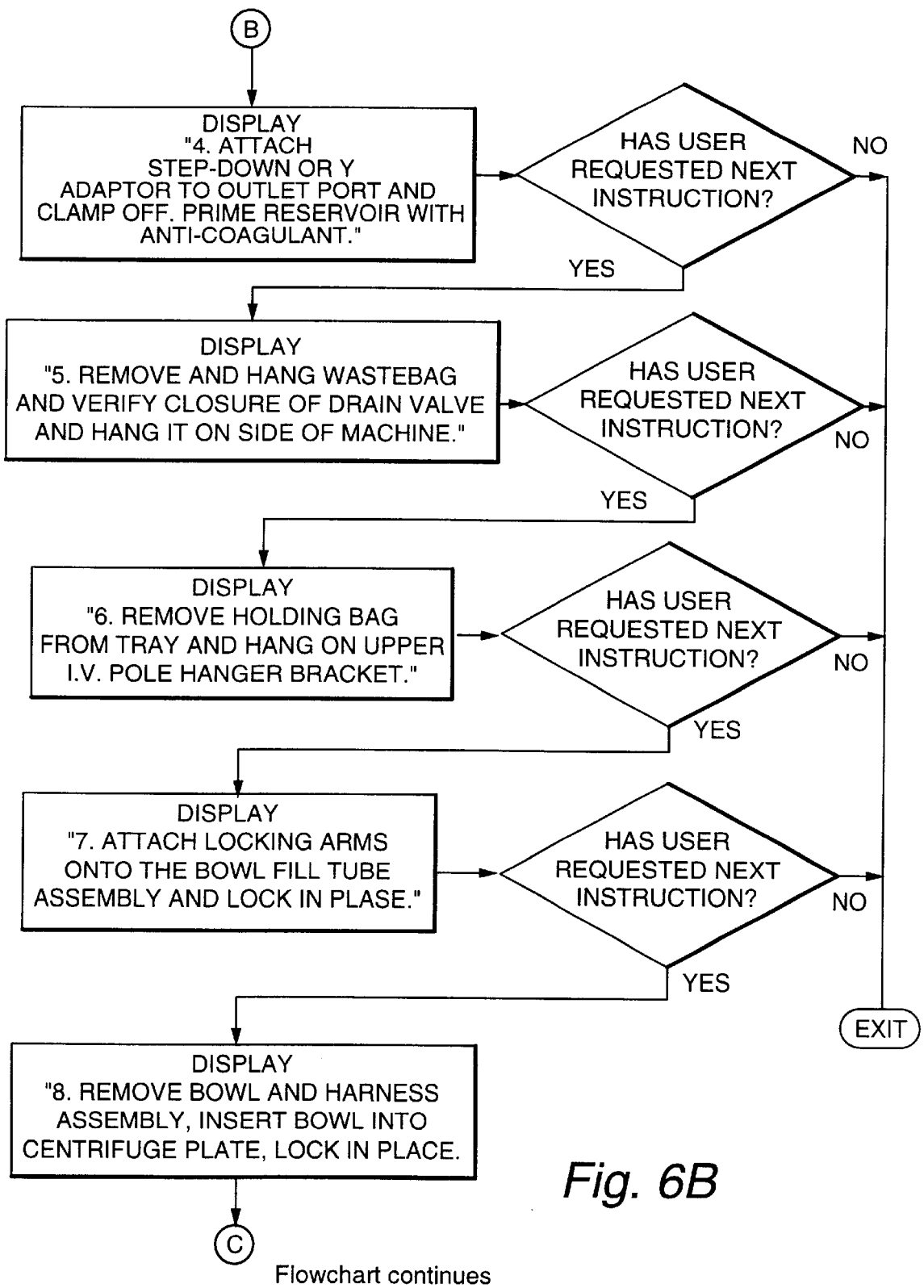
Figure 6C:
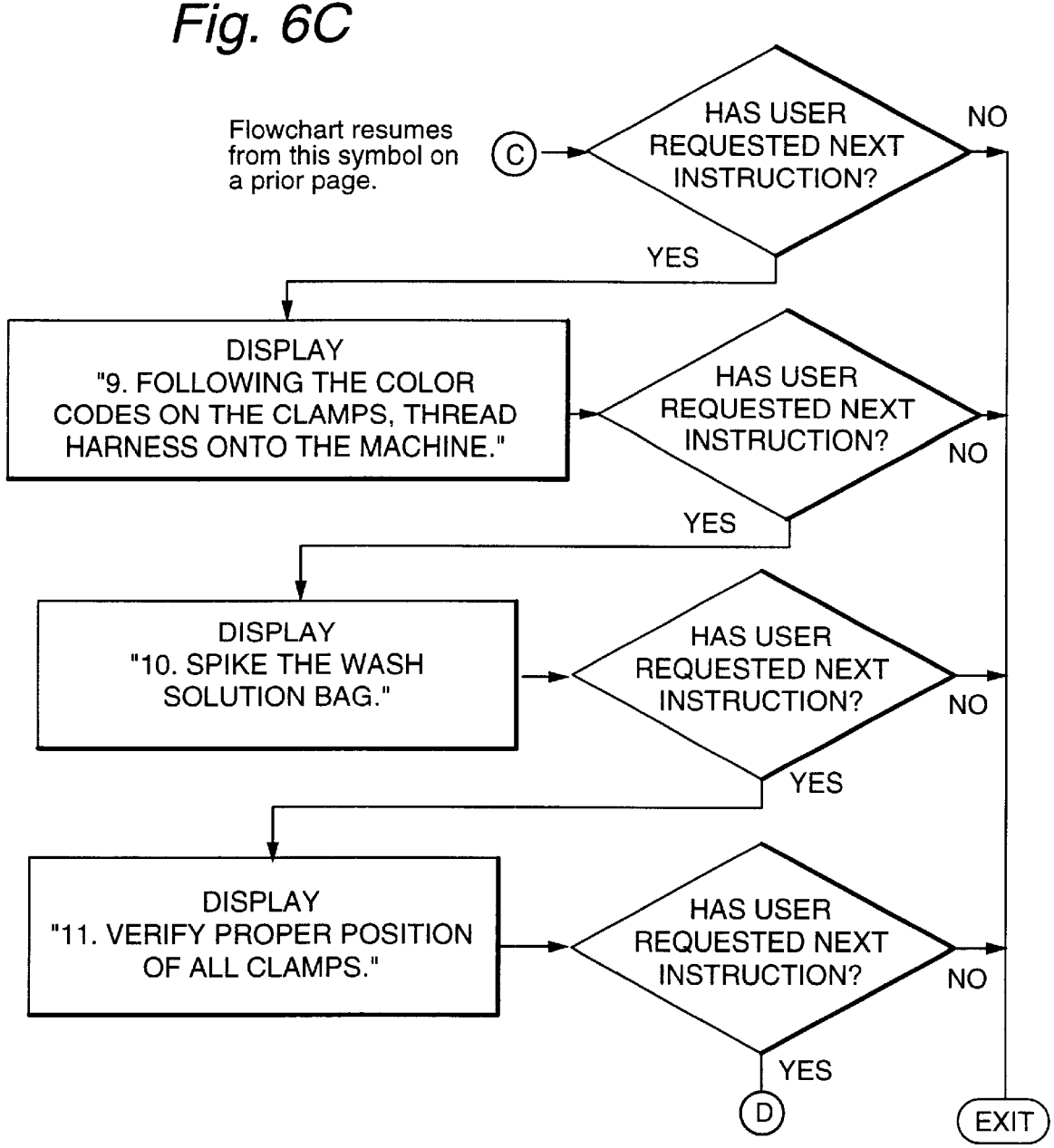
Figure 6D:
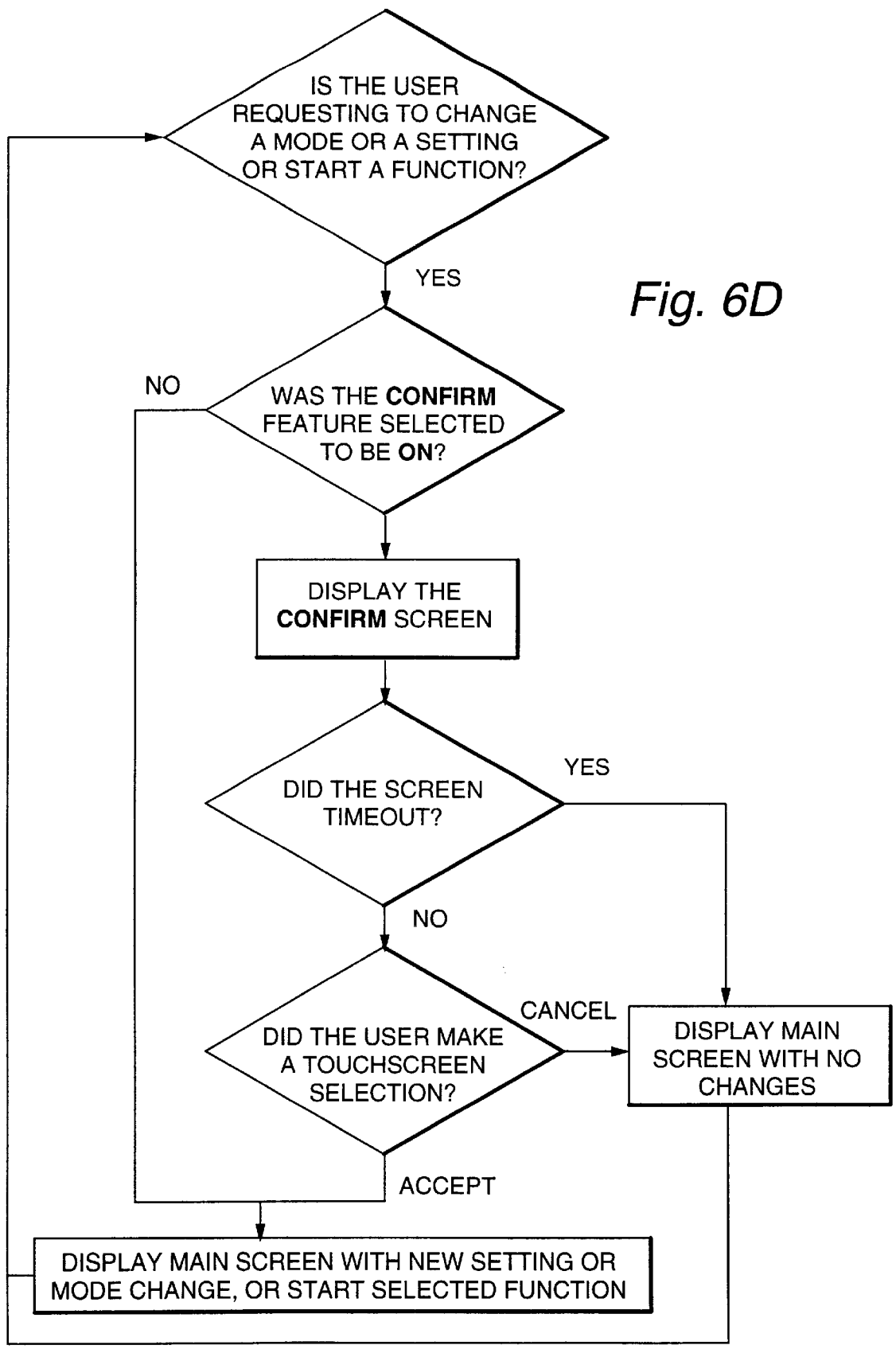
Figure 6E:
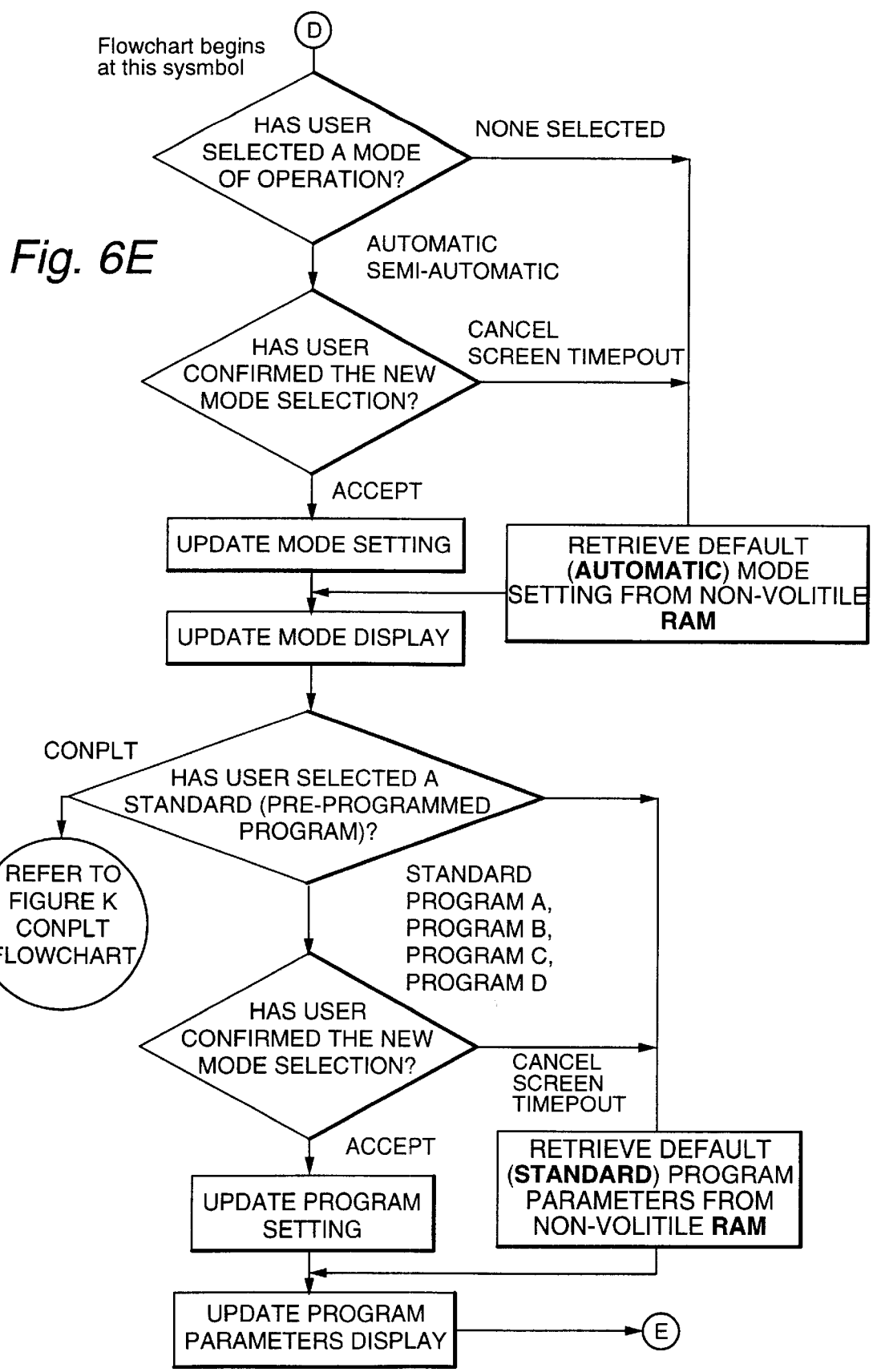
Figure 6F:
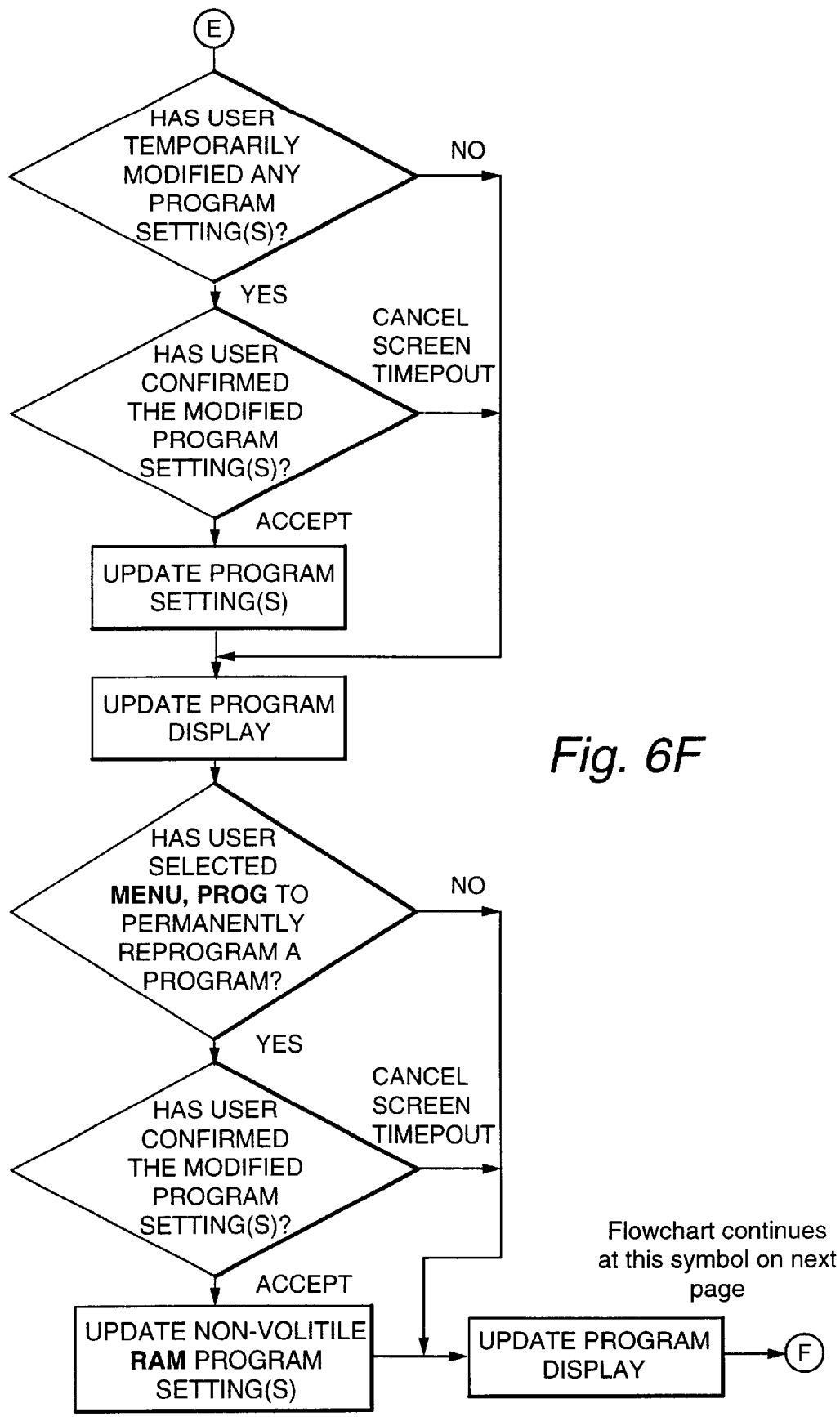
Figure 6G:
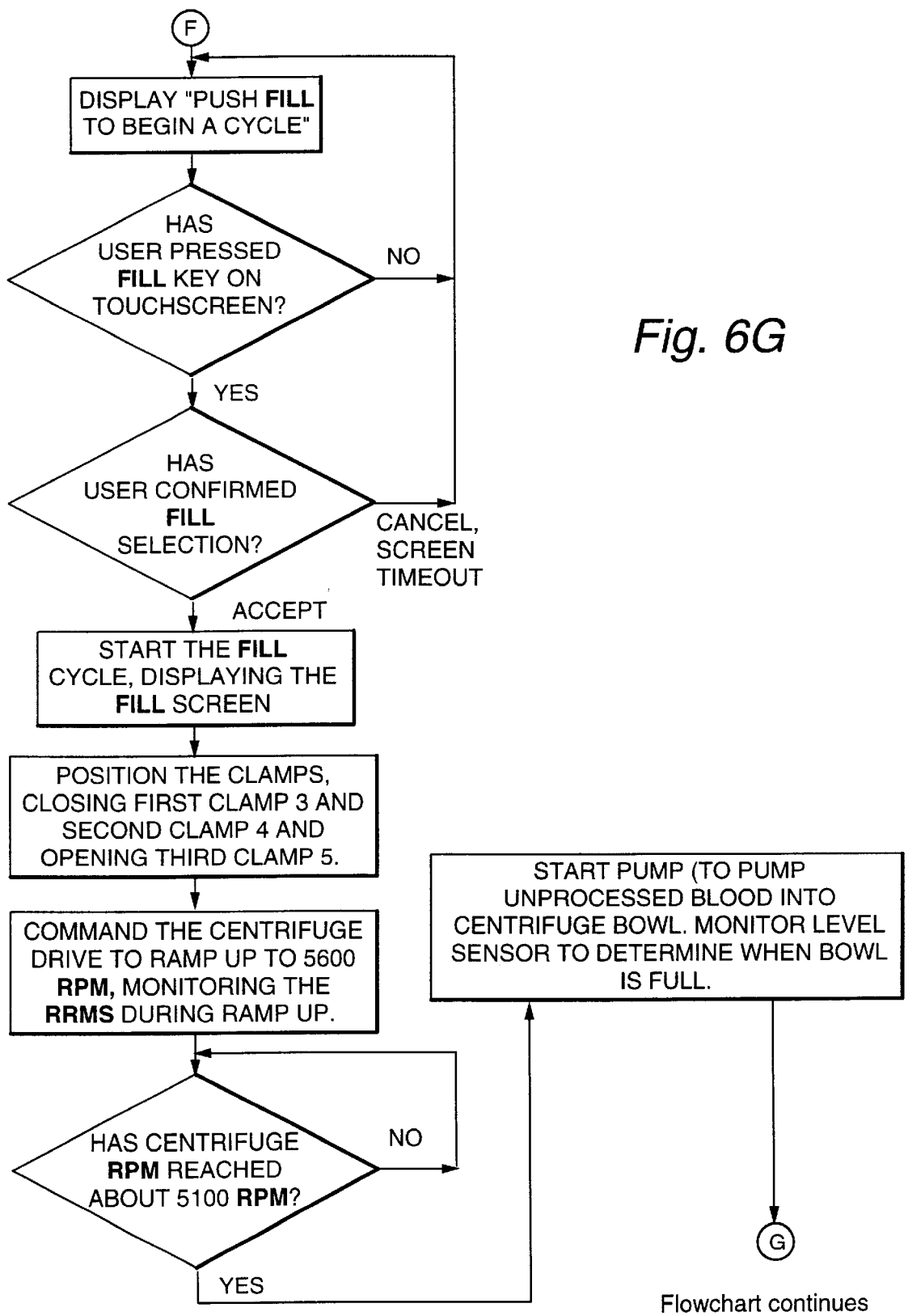
Figure 6H:
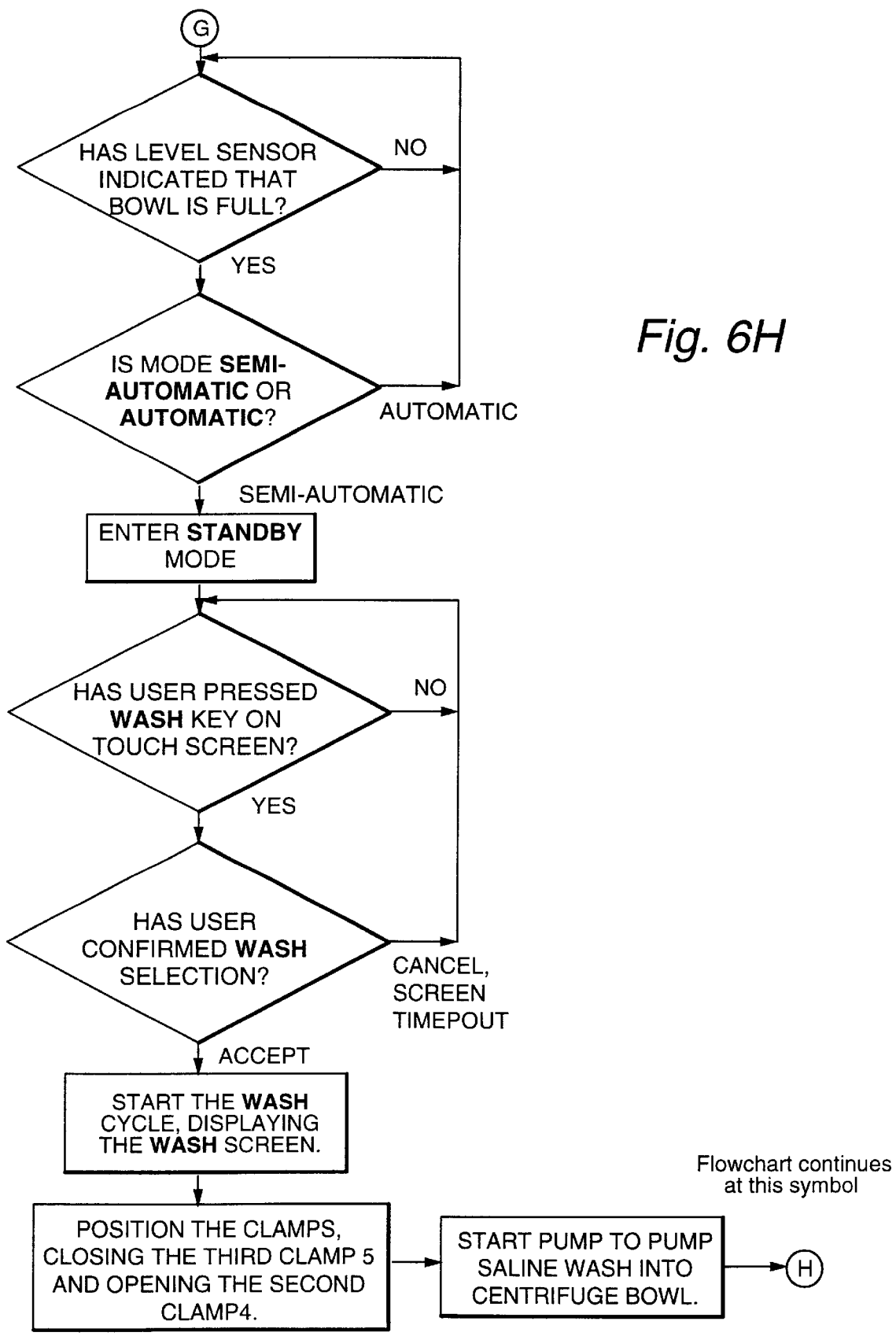
Figure 6I:
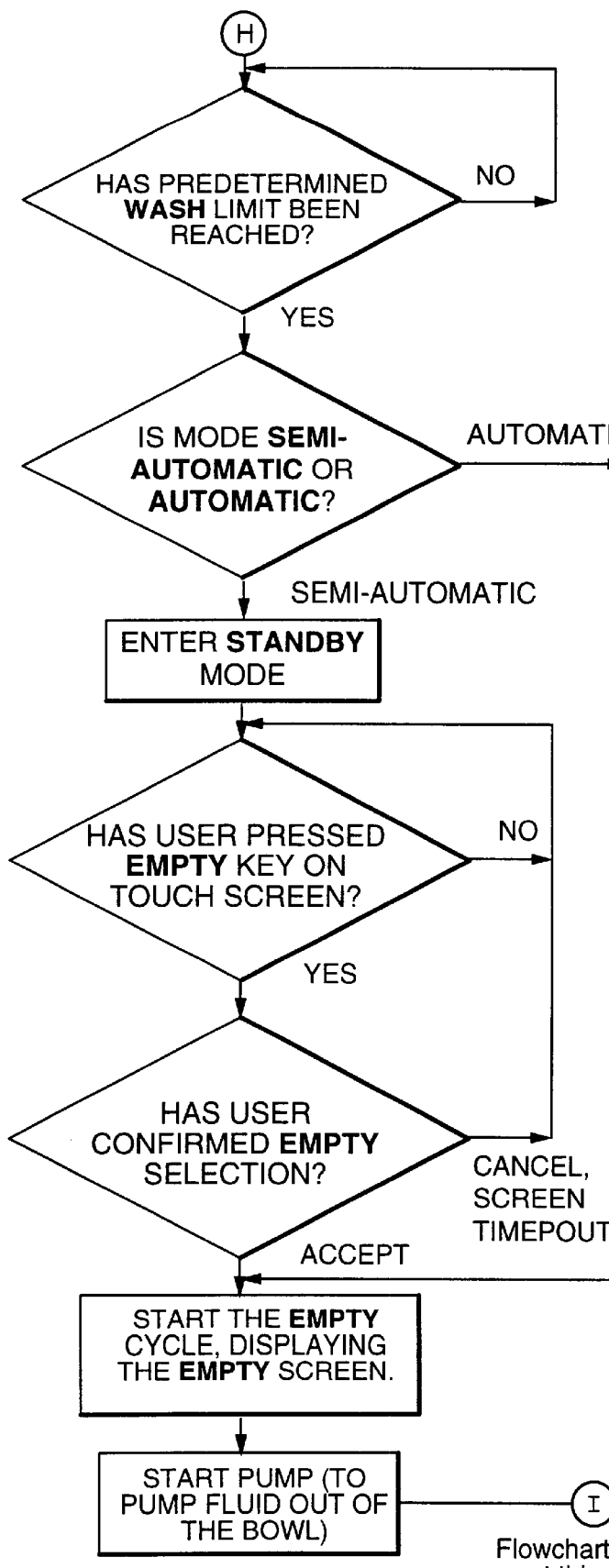
Figure 6J:
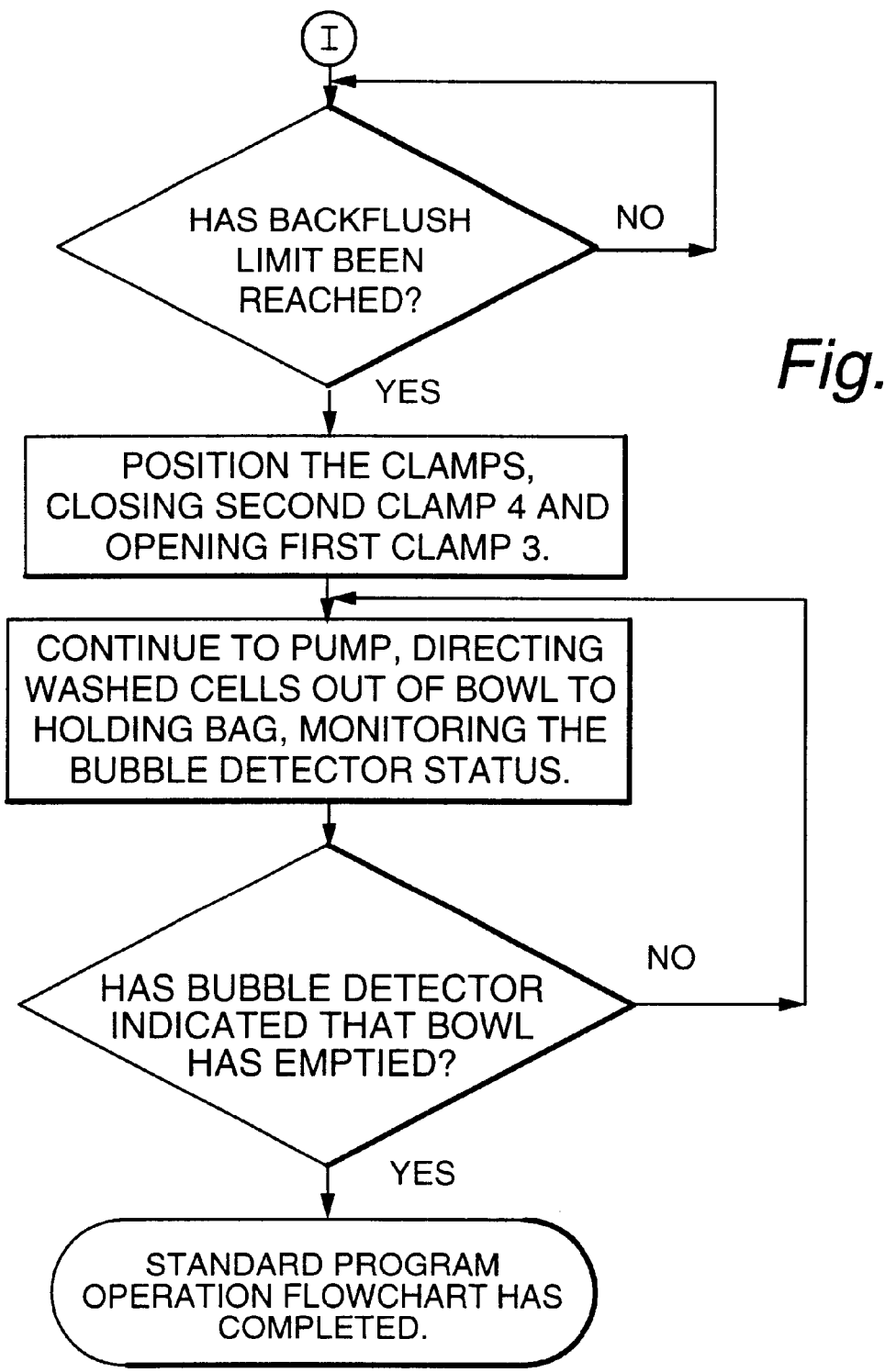
Figure 6K:
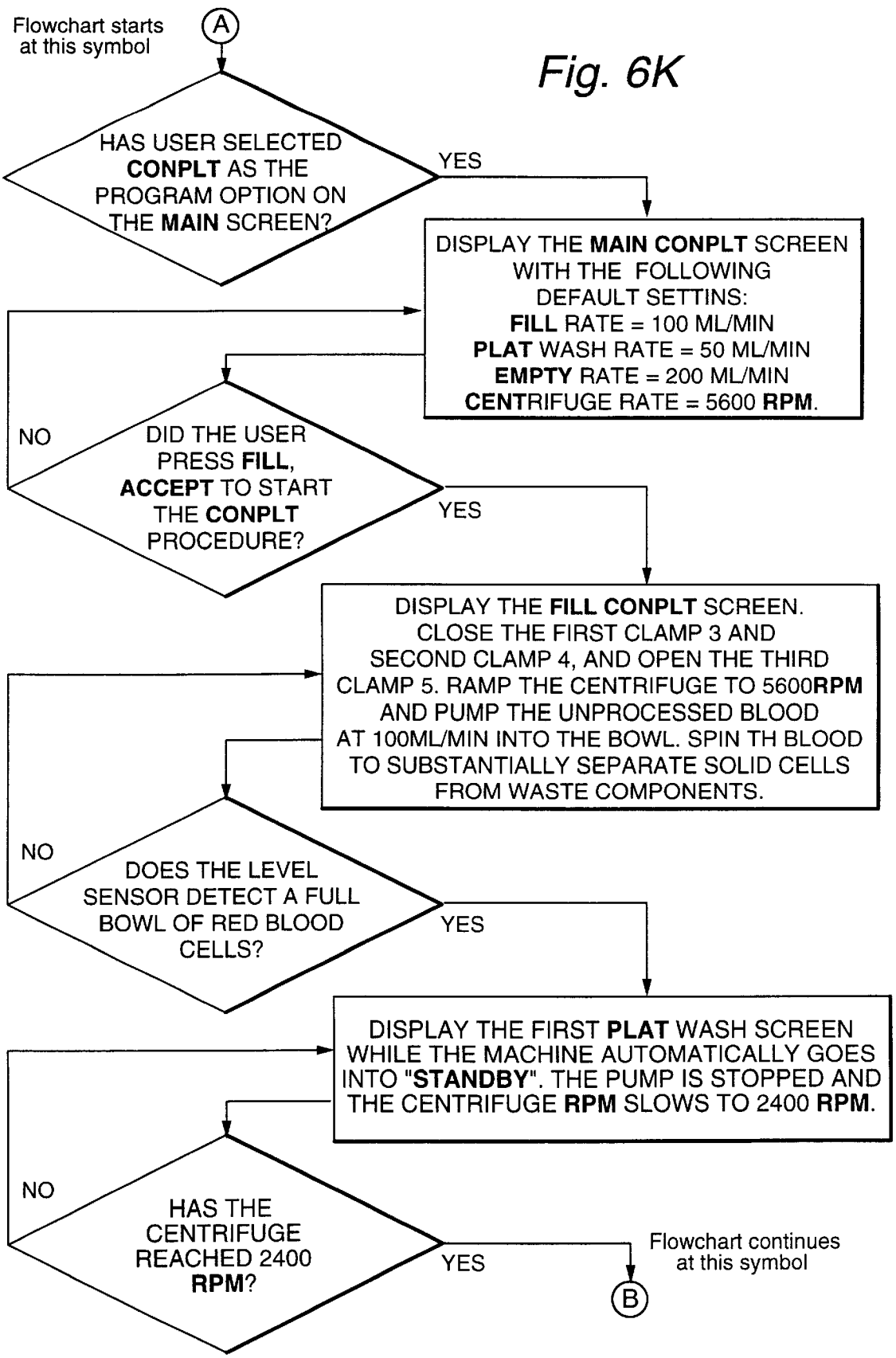
Figure 6L:
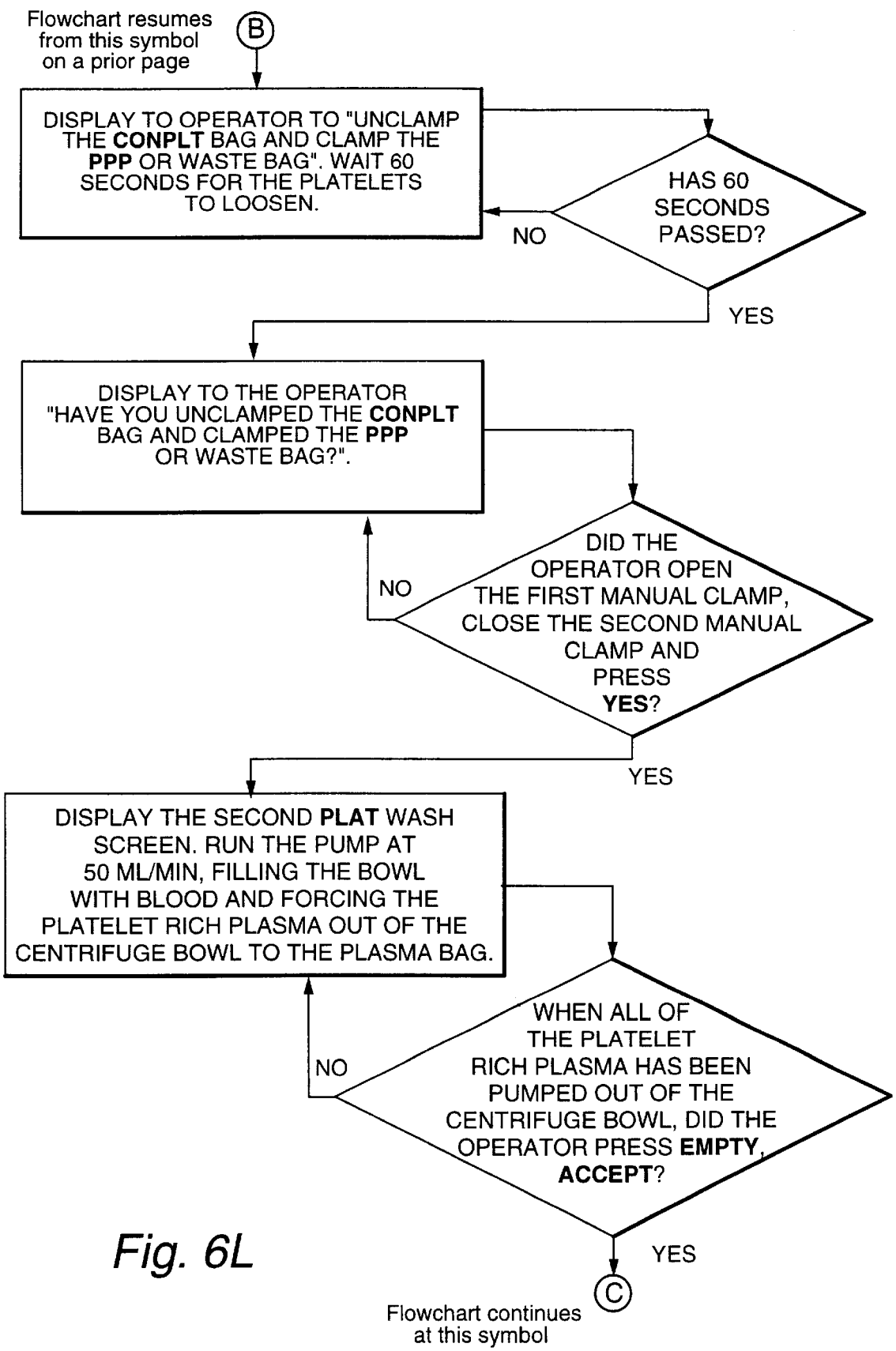
Figure 6M:
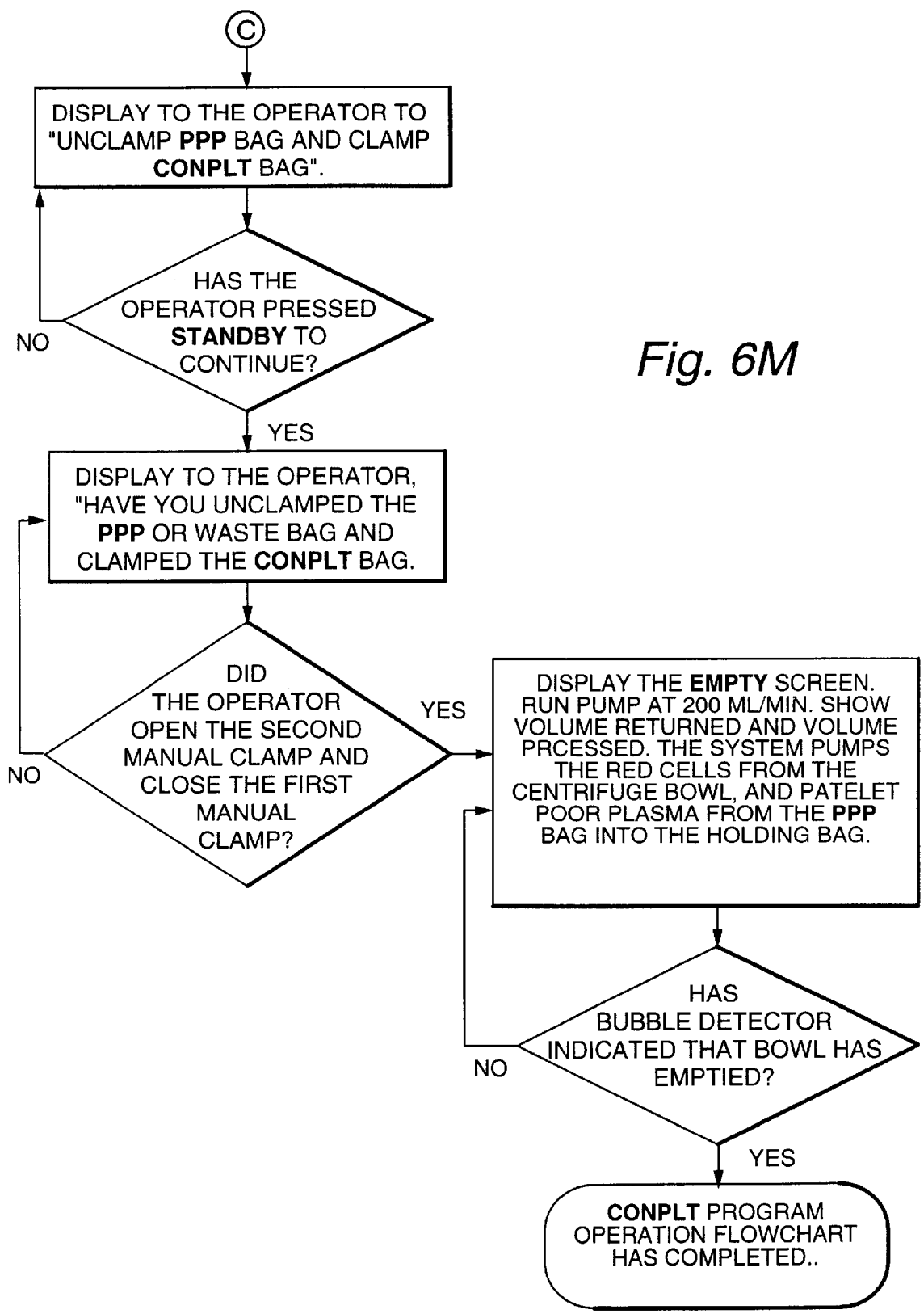

The blood separation system embodying features of the present invention will efficiently provide platelet rich plasma sequestration with the CONPLT Program. Referring to FIG. 5, the setup of the disposable components for platelet rich plasma sequestration is similar to the setup for red cell separation and washing but further includes a second 4-way connector 70, platelet rich plasma tubing 71 connecting to second 4-way connector 70 at a first end, connecting to a platelet rich plasma (PRP) bag 72 at a second end and having a first manual clamp 77 in the middle which is closed during setup, platelet poor plasma tubing 73 connecting to second 4-way connector 70 at a first end, connecting to a platelet poor plasma (PPP) bag 74 at a second end and having a second manual clamp 78 in the middle which is closed during setup, and waste tubing 75 connecting to second 4-way connector 70 at a first end, connecting to waste bag 29 at a second end and having a third manual clamp 79 in the middle which is opened during setup. For platelet rich plasma sequestration the second end of centrifuge exit tubing 28 connects to 4-way connector 70 instead connecting to the waste bag 29 as in the standard setup.

Platelet rich plasma sequestration begins with a fill cycle identical to the fill cycle described above for the standard blood processing procedure. The fill cycle starts with closing first clamp 3 and second clamp 4, and opening third clamp 5. The centrifuge drive means 11 begins to rotate, spinning centrifuge bowl 27. When centrifuge 7 reaches about 5100 rpm pump 2 starts to pump unprocessed blood into centrifuge bowl 27. As the centrifuge bowl 27 fills with blood, the heavier red cells are forced to the outside of centrifuge bowl 27 by centrifugal force while the lighter, undesirable components of the blood are forced inward, up and out of centrifuge bowl 27 through centrifuge exit tubing 28 to waste bag 29. If conservation of platelet poor plasma is desired, when the effluent reaches the first end of centrifuge exit tubing 28, the operator places the blood separation system in "STANDBY" mode, opens second manual clamp 78, closes third manual clamp 79 and releases "STANDBY" mode. When level sensor 55 detects that centrifuge bowl 27 is full of red cells the fill cycle ends.

At the end of the fill cycle the autotranfusion system automatically goes into "STANDBY" mode, slows the centrifuge 7 speed to about 2400 rpm, and displays the messages "Wait 60 seconds to loosen platelets" and "Unclamp PRP bag, then clamp PPP bag" on display 64. The operator will manually open first manual clamp 77 and close second manual clamp 78. After 60 seconds the platelet rich plasma separates from the red cells and moves to the inside top of centrifuge bowl 27. The autotranfusion system displays the message "Have you unclamped the PRP bag and clamped the PPP bag?" on display 64. When the operator confirms opening first manual clamp 77 and closing second manual clamp 78, the autotranfusion system will again begin pumping blood into centrifuge bowl 27, forcing the platelet rich plasma out of centrifuge bowl 27, through centrifuge exit tubing 28, second 4-way connector 70 and platelet rich plasma tubing 71, to platelet rich plasma bag 72.

When all of the platelet rich plasma has been pumped out of centrifuge bowl 27 and centrifuge exit tubing 28 begins to fill with red cells, the operator presses "EMPTY" then "ACCEPT" on touchscreen 65. The blood separation system will display the message "Unclamp PPP bag and clamp PRP bag" and "Press STANDBY to continue" on display 64. After the operator presses "STANDBY", the blood separation system will display the message "Have you unclamped PPP bag and clamp PRP bag?" on display 64. The operator opens second manual clamp 78, closes first manual clamp 77 and presses "YES" on touchscreen 65. The blood separation system pumps the red cells from the centrifuge bowl 27 and platelet poor plasma from platelet poor plasma bag 74 into holding bag 24, completing the platelet rich plasma sequestration.

Although the present invention has been described with a certain degree of particularity, it is understood that the present disclosure has been made by way of example and that changes in details of structure may be made without departing from the spirit thereof.

What is claimed is:

1. A method of sequestering platelet rich plasma from blood comprising the steps of:

spinning an empty centrifuge bowl at a first rate that is sufficiently high speed to substantially separate plasma from solid cells of said blood, pumping said blood into said bowl while said bowl is spinning at said first rate so that said blood is separated into said plasma and said solid cells, and said plasma is pumped out of said bowl, stopping said pumping of said blood into said bowl when said bowl is full of said solid cells, after stopping said pumping, spinning said bowl for a predetermined time at a slower second rate that is sufficient to allow platelets to elute from said solid cells, and after said predetermined time, resuming pumping said blood into said bowl to pump said platelets out of said bowl into a collector.

2. A method of sequestering platelet rich plasma from blood in a centrifugal bloods separator comprising the steps of:

spinning said blood separator at a first speed that is sufficiently high to substantially separate solid cells from waste components of said blood while pumping said blood into said blood separator at a first pump rate until said blood separator is full of said solid cells, then stopping pumping said blood, then spinning said blood separator at a slower second speed that is sufficient to allow platelets to elute from said solid cells for a predetermined time, and then collecting said platelet rich plasma from said blood separator.

3. A method of sequestering platelet rich plasma from blood as set forth in claim 2 wherein said first speed is about 5600 rpm, said first pump rate is 100 ml/min., said second speed is about 2400 rpm, and said predetermined time is about 60 seconds.

4. A method of sequestering platelet rich plasma from blood as set forth in claim 2 wherein said step of collecting said platelet rich plasma includes the step of pumping said blood into said blood separator at a second pump rate to force said platelet rich plasma out of said blood separator into a platelet rich plasma collection bag.

5. A method of sequestering platelet rich plasma from blood as set forth in claim 4 wherein said second pump rate is about 50 ml/min.

* * * * *